US006949256B2

(12) United States Patent
Fonkwe et al.

(10) Patent No.: US 6,949,256 B2
(45) Date of Patent: Sep. 27, 2005

(54) NON-GELATIN CAPSULE SHELL FORMULATION

(75) Inventors: Linus G. Fonkwe, High Point, NC (US); Don A. Archibald, Jamestown, NC (US); Aristippos Gennadios, Greensboro, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 174 days.

(21) Appl. No.: 10/051,201

(22) Filed: Jan. 18, 2002

(65) Prior Publication Data

US 2003/0138482 A1 Jul. 24, 2003

(51) Int. Cl.$^7$ .............................. A61K 9/48; C08B 37/00
(52) U.S. Cl. .................. 424/451; 106/162.1; 536/1.11; 514/54
(58) Field of Search ........................ 424/451; 536/1.11; 106/162.1; 514/54

(56) References Cited

U.S. PATENT DOCUMENTS

| | | | |
|---|---|---|---|
| 2,802,000 A | 8/1957 | Caldwell ................. 260/233.3 |
| 2,813,093 A | 11/1957 | Caldwell ................. 260/233.3 |
| 2,825,727 A | 3/1958 | Caldwell ................. 260/233.3 |
| 3,058,827 A | 10/1962 | Graham ........................ 96/111 |
| 3,329,509 A | 7/1967 | Julius ........................... 99/171 |
| 3,499,962 A | 3/1970 | Wurzburg et al. ............. 424/35 |
| 3,607,394 A | 9/1971 | Germino ...................... 127/32 |
| 3,865,603 A | 2/1975 | Szymanski et al. ......... 106/130 |
| 3,956,173 A | 5/1976 | Towle ......................... 252/316 |
| 3,962,482 A | 6/1976 | Comer et al. ............... 426/575 |
| 4,009,291 A | 2/1977 | Mitchell et al. ............. 426/548 |
| 4,026,986 A | 5/1977 | Christen et al. ............. 264/301 |
| 4,129,134 A | 12/1978 | Hind et al. ..................... 131/2 |
| 4,231,803 A | 11/1980 | Bovier et al. ............... 106/213 |
| 4,276,320 A | 6/1981 | Moirano ...................... 426/575 |
| 4,600,439 A | 7/1986 | Schneider et al. .......... 106/133 |
| 4,615,897 A | 10/1986 | Brown et al. ............... 426/576 |
| 4,632,848 A | 12/1986 | Gosset et al. ............... 427/154 |
| 4,760,129 A | 7/1988 | Haering et al. ............. 528/481 |
| 4,795,642 A | 1/1989 | Cohen et al. ............... 424/455 |
| 4,804,542 A | 2/1989 | Fischer et al. .............. 424/456 |
| 4,935,243 A | 6/1990 | Borkan et al. .............. 424/441 |
| 5,002,934 A | 3/1991 | Norton et al. ................ 514/54 |
| 5,089,307 A | 2/1992 | Ninomiya et al. .......... 428/35.2 |
| 5,146,730 A | 9/1992 | Sadek et al. .................. 53/454 |
| 5,334,640 A | 8/1994 | Desai et al. .................. 524/56 |
| 5,342,626 A | 8/1994 | Winston, Jr. et al. ....... 424/461 |
| 5,393,054 A | 2/1995 | Rouffer ......................... 273/58 |
| 5,451,673 A | 9/1995 | Fishman et al. ............ 536/123 |
| 5,459,983 A | 10/1995 | Sadek et al. .................. 53/560 |
| 5,484,598 A | 1/1996 | Schurig et al. .............. 424/401 |
| 5,550,178 A | 8/1996 | Desai et al. .................. 524/56 |
| 5,554,385 A | 9/1996 | Stroud ......................... 424/456 |
| 5,620,757 A | 4/1997 | Ninomiya et al. .......... 428/34.8 |
| 5,656,294 A | 8/1997 | Friend et al. ............... 424/465 |
| 5,726,008 A | 3/1998 | Maskasky ................... 430/569 |
| 5,756,123 A | 5/1998 | Yamamoto et al. ......... 424/451 |
| 5,804,243 A | 9/1998 | Loh et al. .................... 426/552 |
| 5,811,388 A | 9/1998 | Friend et al. .................. 514/2 |
| 5,817,323 A | 10/1998 | Hutchinson et al. ........ 424/439 |
| 5,932,639 A | 8/1999 | Eden et al. ................... 524/48 |
| 5,962,053 A | 10/1999 | Merritt, II .................... 426/93 |
| 5,976,586 A | 11/1999 | Feller .......................... 426/89 |
| 6,030,641 A | 2/2000 | Yamashita et al. .......... 424/451 |
| 6,063,915 A | 5/2000 | Hansen et al. .............. 536/114 |
| 6,066,368 A | 5/2000 | Billmers et al. ......... 427/393.4 |
| 6,143,324 A * | 11/2000 | Michaud et al. ............ 424/465 |
| 6,146,570 A | 11/2000 | Stern .......................... 264/141 |
| 6,183,845 B1 | 2/2001 | Ikemoto ...................... 428/213 |
| 6,210,709 B1 | 4/2001 | Laba et al. .................. 424/451 |
| 6,214,376 B1 | 4/2001 | Gennadios .................. 424/451 |
| 6,331,205 B1 | 12/2001 | Paris et al. ............... 106/205.9 |
| 6,340,473 B1 | 1/2002 | Tanner et al. ............... 424/451 |
| 6,375,981 B1 | 4/2002 | Gilleland et al. ........... 424/452 |
| 6,517,865 B2 | 2/2003 | Cade et al. .................. 424/451 |
| 6,528,088 B1 | 3/2003 | Gilleland et al. ........... 424/451 |
| 6,582,727 B2 | 6/2003 | Tanner et al. ............... 424/451 |
| 6,607,748 B1 * | 8/2003 | Lenaerts et al. ............ 424/464 |
| 6,745,546 B2 | 6/2004 | Tanner et al. ................. 53/560 |
| 6,790,495 B1 | 9/2004 | Tomka et al. .............. 428/35.2 |
| 2002/0081331 A1 | 6/2002 | Tanner et al. ............... 424/451 |
| 2002/0142031 A1 | 10/2002 | Gilleland et al. |
| 2002/0155200 A1 | 10/2002 | Macquarrie ................. 426/250 |
| 2002/0187185 A1 | 12/2002 | Jones ........................ 424/452 |
| 2003/0085487 A1 | 5/2003 | Von Wendorff ............. 370/216 |
| 2004/0060258 A1 | 4/2004 | Stolz .......................... 53/266.1 |
| 2004/0071808 A1 | 4/2004 | Peter et al. ............... 425/133.5 |

FOREIGN PATENT DOCUMENTS

| | | |
|---|---|---|
| CA | 2243227 | 5/1999 |
| EP | 0 169 319 B1 | 1/1986 |
| EP | 0328317 | 8/1989 |

(Continued)

OTHER PUBLICATIONS

Ionnis Arvanitoyannis, et al., "Edible films made from sodium caseinate, starches, sugars or glycelrol. Part 1", *Carbohydrate Polymers*, 31:179–192 (1996).

(Continued)

*Primary Examiner*—James O. Wilson
*Assistant Examiner*—Ganapathy Krishnan
(74) *Attorney, Agent, or Firm*—Womble Carlyle Sandridge & Rice, PLLC

(57) ABSTRACT

A film-forming hydrocolloid composition comprising kappa carrageenan, iota carrageenan, a bulking agent, plasticizer and water is described. The ratio of bulking agent to total carrageenan is from about 1:1 to 20:1. Kappa carrageenan is present in an amount of less than or equal to 50% by weight of total carrageenan present. To form the composition, all dry materials are mixed and added to a heated mixture of all liquid materials. The final mixture is heated until a composition free of particulate materials is formed. The formed composition can be cast or extruded into ribbons, films, sheets, tubes or the like, for encapsulating wet or dry materials including medicinal dosage forms, nutritional supplements, cosmetics, bath oils and gels, and paint balls.

8 Claims, No Drawings

FOREIGN PATENT DOCUMENTS

| | | |
|---|---|---|
| EP | 0 408 503 B1 | 1/1991 |
| EP | 0 409 782 B1 | 1/1991 |
| EP | 0 409 788 B1 | 1/1991 |
| EP | 0 471 558 A2 | 2/1992 |
| EP | 0 400 484 B1 | 1/1994 |
| EP | 0622408 | 2/1994 |
| EP | 0 409 781 B1 | 6/1994 |
| EP | 0 761 691 A2 | 3/1997 |
| EP | 0 547 551 B1 | 11/1997 |
| EP | 0 633 896 B1 | 6/1998 |
| EP | 1103254 | 5/2001 |
| EP | 1216680 | 6/2002 |
| EP | 1258242 | 11/2002 |
| JP | 50105766 | 8/1975 |
| JP | 50105767 | 8/1975 |
| JP | 63118229 | 5/1988 |
| JP | 3121825 | 5/1991 |
| JP | 3127945 | 5/1991 |
| JP | 3190709 | 8/1991 |
| JP | 4089841 | 3/1992 |
| JP | 07196478 | 1/1995 |
| JP | 7062160 | 3/1995 |
| JP | 2000127225 | 5/2000 |
| WO | WO94/25493 | 11/1994 |
| WO | WO 97/49762 | 12/1997 |
| WO | WO 99/07347 | 2/1999 | ............ A61K/9/48 |
| WO | WO 00/10538 | 3/2000 | ............ A61K/9/48 |
| WO | WO 00/18835 | 4/2000 |
| WO | WO 01/03677 A1 | 1/2001 |
| WO | WO 01/03677 * | 1/2001 | ............ A61K/9/48 |
| WO | WO 01/37817 A1 | 5/2001 |
| WO | WO 01/91721 A2 | 12/2001 |
| WO | WO 01/91721 * | 12/2001 | ............ A61K/9/00 |
| WO | WO/02/007711 | 1/2002 |
| WO | WO/02/49572 | 6/2002 |
| WO | WO 02/053088 | 7/2002 |
| WO | WO/03/009832 | 2/2003 |

OTHER PUBLICATIONS

Ioannis Arvanitoyannis, et al., "Biodegradable films made from low–density polyethylene (LDPE), rice starch and potato starch for food packaging applications: Part 1", *Carbohydrate Polymers*, 36:89–104 (1998).

Eleni Psomiadou, et al., "Edible films made from natural resources; microcrystalline cellulose (MCC), methylcellulose (MC) and corn starch and polyols—Part 2", *Carbohydrate Polymers*, 31:193–204 (1996).

*Food Product Design*, Hegenbart article "Bind for Glory: Designing Foods Using Gums," pp. 21, 24, 26, 29, 32, 35, 38, 42, (Jan. 1993).

Chandrasekaran, R., et al., "Molecular architectures and functional properties of gellan gum and related polysaccharides," *Trends in Food Science & Technology*, vol. 6, pp. 143–148, (May 1995).

Hegenburt, S., "Understanding Carrageenan," *Food Product Design*, vol. 4(3), pp. 109–120, (Jun. 1994).

Sanderson, G. R. et al., "Gellan Gum," *Food Technology*, pp. 63–70 (Apr. 1983).

Nishinari, K et al., "Characterization and properties of gellan–k–carrageenan mixed gels," *Food Hydocollids*, vol. 10(3), pp. 277–283, (1996).

Oakenfull, D. et al., "Rheological and thermal properties of milk gels formed with k–carrageenan and sodium caseinate," *Food Hydrocolloids*, vol. 13, pp. 529, (1999).

Morris, V. J. et al., "Gelation of polysaccharides," *Functional Properties of Food Macromolecules*, p. 168, available as of the filing date.

"VegaGels: Technical Information," Swiss Caps, 2000.

Wilkinson, P.K., "Softgels: manufacturing and considering, in Specialized Drug Delivery Systems," *Manufacturing and Production Technology*, Praveen Tyle, Ed., p. 431, 1990.

Krochta, et al., "Edible and Biodegradable Polymer Films: Challenges and Opportunities," *Food Technology* 51:61–74 (1997).

Lourdin, et al., "Influence of Amylose Content on Starch Films and Foams," *Carbohydrate Polymers* 27:261–270 (1995).

Kester, et al., "Edible Films and Coating: A Review," *Food Technology* 40:47–59 (1986).

Shih, "Effects of Additives on the Development of Edible Fims," *Chemistry of Novel Foods*, Chapter 14, 1995 International Chemical Congress of Pacific Basin Societies, Honolulu, Hawaii (Dec. 17–22, 1995).

Bergthaller, et al., "Potato Starch Technology,"*Starch/Stärke* 51:235–242 (1999).

BeMiller, et al., "Carbohydrates," *Food Chemistry*, pp. 205–223 no date.

"The Birth of a Paintball," *R.P. Scherer Paintballs—How Paintballs are...*, pp. 1–2 (1998).

Picullel, "Gelling Carrageenans," *Food Polysaccharides and Their Applications*, pp. 205, 210–212, 233–234 (1995).

Rochas et al., "Relation Between the Molecular Structure and Mechanical Properties of Carrageenan Gels," *Carbohydrates Polymers* 10:115–127 (1989).

Hermansson, et al., "Effects of Potassium, Sodium and Calcium on the Microstructure and Rheological Behaviour of Kappa–Carrageenan Gels," *Carbohydrate Polymers*, 16:297–320 (1991).

Arvanitoyannis, et al., "Edible Films Made from Hydroxypropyl Starch and Gelatin and Plasticized by Polyols and Water," *Carbohydrate Polymers* 36:105–119 (1998).

Derwent Abstract WO 9923118 A1.

Derwent Abstract JP 5148388 A.

Derwent Abstract WO 9304670 A.

Derwent Abstract JP 5004914 A

Derwent Abstract WO 9218014 A.

Derwent Abstract WO 9206672 A.

Derwent Abstract EP 471558 A.

Derwent Abstract WO 9200731 A.

Derwent Abstract EP 400484 A.

Derwent Abstract JP 63170310 A.

Derwent Abstract EP 273823 A.

Derwent Abstract JP 61009258 A.

Derwent Abstract JP 60037966 A.

Derwent Abstract JP 72023384 B.

U.S. Appl. No. 09/585,846, filed Jun. 1. 2000 (no copy available to applicant).

* cited by examiner

NON-GELATIN CAPSULE SHELL FORMULATION

FIELD OF THE INVENTION

The present invention relates to the field of film-forming or gel-forming compositions, and more particularly to substitutes for mammalian-based gel forming materials used in the manufacture of softgels and gelcaps.

BACKGROUND OF THE INVENTION

Gelatin has a wide range of commercial utility. For example, gelatin is used in wet processed photographic emulsions, pharmaceutical dosage forms, cosmetics (binder), and a wide range of food products. Gelatin has many useful physical and chemical properties that support this broad range of utility.

Gelatin is manufactured by the hydrolysis of animal by-products that contain collagen. This is usually found in animal bones, skins, and connective tissue. The collagen containing material is heated in water and the liquor produced is concentrated and dried, leaving behind the colorless or pale yellow protein that constitutes the hydrophilic colloid material known as gelatin.

The primary sources of gelatin are from bovine and swine animals. Additionally, fish and poultry are alternative small volume sources of gelatin. The source of gelatin can be a problem for potential areas of use or for particular consumers. Large groups around the world choose not to ingest any products of pigs (e.g., vegetarians, Hebrews, and Muslims) or the products of beef (e.g., vegetarians and Hindus). As medication and/or diet supplements are provided in gelatin capsules without any indication of the source of the gelatin, the use of capsules is restricted in areas where religious beliefs question the source of the gelatin. Additionally, due to reported possibilities of cross-contamination of diseases among species, for example bovine spongiform encephalopathy ("BSE" or "Mad Cow Disease"), the use of uncontrolled by-products from animals has lost some level of commercial acceptance. In short, there is a need for replacement compositions for gelatin that are not derived from animal sources.

Carrageenan is a natural hydrocolloid, more particularly a polysaccharide hydrocolloid, which is derived from red seaweed, particularly of the species Rhodophycea. Carrageenan is a carbohydrate polymer of repeating galactose and 3,6-anhydrogalactose (sugar) units that is linear and without significant numbers of branches or substitutions. Most, if not all, of the galactose units on a carrageenan molecule possess a sulfated ester group. The exact position of the sulfate groups, the cations on the sulfate groups, and the possible presence of an anhydrous bridge on the molecule differentiate the various types of carrageenan.

There are five distinct types of carrageenan, each of which behaves differently and has distinct properties. The types of carrageenan are iota, kappa, lambda, mu and nu carrageenan. These types of carrageenan can significantly vary in properties. For example, lambda carrageenan in solution is unable to associate into a structure, and therefore is unable to form a gel, but nonetheless acts as a thickener. Both kappa and iota carrageenan, the predominant carrageenan types, are able to form gels. Kappa carrageenan is known to form strong gels in the presence of potassium cations. However, kappa carrageenan gels tend to be brittle and exhibit syneresis (exudation of the liquid portion of the gel). Iota carrageenan tends to react strongly to calcium cations and forms a weaker and more flexible gel than kappa carrageenan. Iota carrageenan is not as susceptible to syneresis as kappa carrageenan. Mu and nu carrageenan are thought to be precursors of kappa carrageenan and iota carrageenan, respectively, and may be present only in very small quantities as impurities in pure kappa and iota carrageenan. Mu and nu carrageenan are not of commercial importance.

The type of carrageenan used affects the physical properties of the final gel or film. WO 99/07347 and WO 01/03677 describe gel forming compositions that have iota carrageenan as the sole gelling agent. Despite the fact that kappa carrageenan is also able to gel, these publications teach that kappa carrageenan is detrimental when the end product desired is a film for capsule manufacture. The phenomenon of syneresis and the fact that kappa carrageenan forms brittle gels are cited as reasons for avoiding the use of kappa carrageenan in such films.

When forming a film for subsequent use in medicinal, cosmetic, or nutritional capsule manufacture, the resultant physical properties of sealability, extensibility, and tensile strength are important. Thus, a gelling composition comprising carrageenan must provide adequate physical properties useful in manufacturing. Kappa carrageenan is a less expensive starting material as compared to iota carrageenan. Thus, it would be beneficial to develop a gel- or film-forming composition comprising kappa carrageenan and iota carrageenan, wherein the resultant film provides the requisite physical properties for capsule manufacture.

SUMMARY OF THE INVENTION

The present invention is a non-animal based hydrocolloid film-forming composition for use in the manufacture of encapsulated dosage forms. The film-forming composition comprises:

iota carrageenan in an amount from about 1% to about 15% by weight of the composition;

a bulking agent wherein the ratio of bulking agent:total carrageenan is from at least about 1:1 to about 20:1;

kappa carrageenan in an amount less than or equal to 50% by weight of total carrageenan;

a plasticizer in an amount of from about 10% to about 50% by weight of the total composition; and water to form 100% by weight of the composition, wherein the total of all carrageenan is in an amount less than or equal to 20% by weight of the composition.

The kappa carrageenan provides gel strength while the iota carrageenan provides flexibility to the film-forming composition.

The composition optionally can include one or more additives as known to practitioners in the art such as an opacifier, preservative, flavorant, colorant and the like.

The composition is formed by mixing iota carrageenan, kappa carrageenan, one or more bulking agents, a plasticizer and water and heating the mixture with stirring until a smooth mixture free of particulates is achieved. Desirably, all dry ingredients, including iota carrageenan, kappa carrageenan and one or more bulking agents are mixed together while all liquid ingredients, including water and plasticizer, are mixed together and heated to at least about 75° C. The dry mix is added to the heated liquid mixture with stirring and further heated to a temperature of no more than about 95° C. with stirring until a smooth mixture free of particulates is achieved. Alternatively, the dry mix and liquid mixture can be fed to an extruder where the dry mix and liquid mix are mixed and heated simultaneously into a smooth mixture free of particulates, then extruded through dies.

These and other aspects of the present invention as disclosed herein will become apparent to those skilled in the art reading the following description of embodiments of the invention. The embodiments as set forth herein do not limit the scope of the invention, which is intended to cover equivalent materials, methods and compositions as known to practitioners in the art, and as set forth in the appended claims.

DETAILED DESCRIPTION OF EMBODIMENTS OF THE INVENTION

Formulations and methods for the manufacturing of non-animal based hydrocolloid film-forming compositions are described. The film-forming composition is used for encapsulation of dosage forms in liquid, solid, gel, paste or suspension form. Such dosage forms can include medicinal, pharmaceutical, nutritional or dietetic drug dosage forms, as well as cosmetics, paints, bath products or other desirably encapsulated dosage forms.

As used herein, the term "softgel" means a soft gelatin capsule, in agreement with the accepted nomenclature adopted by the SoftGel Association. Formerly, the accepted nomenclature was a soft elastic gelatin (SEG) capsule. Generally, a softgel is a one-piece, sealed, soft gelatin (or other film-forming material) shell that contains a solution, a suspension, or a semi-solid paste.

Other encapsulated dosage forms are known to practitioners in the art and include, but are not limited to, caplets such as SOFLET™ gelatin-enrobed hard tablets made by Banner Pharmacaps, Inc.

The phrase "dosage form" as used herein encompasses any material or composition in a form suitable for encapsulation by the film-forming composition described herein. Thus, a dosage form can be a pharmaceutical or nutritional composition, or a cosmetic, paint, soap, bath oil or other desirably encapsulated product. The dosage form can be a solid, liquid, gel, suspension or any other form suitable for encapsulation.

The term "encapsulated dosage form" refers to any dosage form encapsulated with a non-animal hydrocolloid film-forming composition as set forth herein. The encapsulated dosage form can be in any form known to practitioners in the art, such as but not limited to a softgel or caplet.

"Encapsulated" and other forms of the word "encapsulate" as used herein mean placing a dosage form inside of a film-forming composition, such that the dosage form is completely surrounded by the film-forming composition. By methods known to practitioners in the art, the dosage form can be inserted into the film-forming composition in some manner, or the film-forming composition can be wrapped around the dosage form.

A "capsule shell" as used herein refers to the film-forming composition described herein when used to encapsulate a substance such as a drug dosage form.

"Capsule" refers to a softgel, caplet, or any other encapsulated dosage form known to practitioners in the art, or a portion thereof.

The phrase "solids content" as used herein refers to the ratio of the weight of the dry film-forming composition components to the total weight of the composition, expressed as a percentage.

Manufacture of uniform capsule shells requires a film-forming composition that has good "machineability," i.e., it is important that the film-forming composition be able to be brought into contact with rollers or other machine parts during processing without sticking onto these machine parts. However, some stickiness is required for proper seam formation and, in the manufacture of caplets, to improve contact between the encapsulating material and the solid tablet core.

Physical characteristics for proper machineability of the film-forming composition described herein during film formation, capsule shell formation and encapsulation of a dosage form, regardless of the method or machine used, include desirable extensibility, sealability, viscosity and tensile strength at rupture of the film-forming composition as known to practitioners in the art.

The term "extensibility" as used herein defines the increase in length of the film-forming composition set forth herein once formed into a dry film having a moisture content of from about 5% to about 20%, on application of a tensile force (pull). A desirable maximum increase in length at rupture for a 50 mm long film of about 20 mm wide is between about 20 mm and about 80 mm, most desirably between about 35 mm and about 70 mm.

The term "sealability" refers to the ability of one or more film of the film-forming composition set forth herein to fuse together using methods known to practitioners in the art, such as but not limited to the application of heat and/or pressure. The seam that is created in the film upon fusing should be continuous and strong to prevent leakage of encapsulated dosage forms.

The viscosity of the film-forming composition is desirably in the range of from about 100 cP to about 1200 cP, and more desirably in the range of from about 350 cP to about 750 cP, as measured at 90° C. using a mechanical rheometer at a shear rate of 0 to 100 per second in two (2) minutes, a Brookfield viscometer, or other device known to practitioners in the art to measure viscosity.

The tensile strength at rupture of a film made from the film-forming composition set forth herein having a moisture content of between about 5% and about 20% is desirably between about 5 N and about 40 N, most desirably between about 10 N and about 25 N, as measured by methods known to practitioners in the art. One suitable means of measuring the tensile strength at rupture is by use of a TA-XT2 Texture Analyzer by Stable Micro Systems (Surrey, UK).

The film-forming composition comprises a blend of iota and kappa carrageenan, thus overcoming the recognized deficiencies of kappa carrageenan. A film-forming composition having the desired physical properties of extensibility, sealability, viscosity and tensile strength at rupture is provided. The kappa carrageenan provides gel strength while the iota carrageenan provides flexibility to the hydrocolloid film. No additional gelling salts or processing aids, such as surfactants or buffers, are necessary for producing a suitable film-forming composition of the invention. Thus, due to the use of less expensive starting materials and fewer ingredients, the film-forming composition set forth herein provides a more cost effective film-forming material than heretofore available.

The film-forming composition comprises from about 1% to about 15% by weight commercially available iota carrageenan, such as but not limited to TIC Pretested® COLLOID 881M, available from TIC Gums of Belcamp, Md. Other available forms of iota carrageenan as known to practitioners in the art are also suitable for use herein. Desirably, iota carrageenan is present in an amount of from 2.3% to about 10% by weight of the composition, more desirably in an amount of from 2.5% to about 7.5% by weight of the composition.

The film-forming composition also comprises kappa carrageenan in an amount less than or equal to 50% by weight of total carrageenan in the film-forming composition. Desirably, kappa carrageenan is present in an amount of less than or equal to about 100% by weight of iota carrageenan, more desirably in an amount less than about 100% by weight of iota carrageenan, provided the total amount of carrageenan does not exceed 20% by weight of the composition. Kappa carrageenan is present in an amount of from about 0.1% to about 15% by weight of the composition, and more desirably in an amount of from about 0.5% to about 7.5% by weight of the composition. Kappa carrageenan from any commercial source is acceptable, such as TIC Pretested® COLLOID 710H, available from TIC Gums of Belcamp, Md. Other commercial sources of kappa carrageenan as known to practitioners in the art are also suitable for use herein.

A mixture of kappa carrageenan and a glucomannan such as but not limited to konjac flour, as known to practitioners in the art, may be used in place of some or all of the kappa carrageenan in the composition. One example of such a mixture is NUTRICOL® GP751, a commercially available blend of kappa carrageenan and konjac flour, sold by FMC Biopolymer of Philadelphia, Pa. Other blends of kappa carrageenan and glucomannans as known to practitioners in the art are also suitable for use herein in place of some or all of the kappa carrageenan.

The total amount of carrageenan in the composition is less than or equal to about 20% by weight of the composition. Desirably, the total amount of carrageenan is less than or equal to about 10% by weight of the composition.

Other hydrocolloids as known to practitioners in the art optionally can be present in the composition in limited amounts. The total amount of all hydrocolloids, including the carrageenans but excluding bulking agents, desirably does not exceed 22% by weight of the composition. Desirably, such hydrocolloids include viscosity agents that can modify the physical properties of the final gel or film. Practitioners in the art appreciate that adding plant-based hydrocolloids and gums to a film-forming composition can increase the viscosity of the composition. Viscosity agents suitable for use in the composition disclosed herein include, but are not limited to alginates, guar, pectin, locust bean gum, xanthan gum, agar, unmodified starch, modified pregelatinized starch, gellan gum and other viscosity agents known to practitioners in the art. Hydrocolloids acting as viscosity agents are optionally added to the film-forming composition in amounts less than or equal to about 2% by weight of the composition to increase the viscosity of the composition.

The hydrocolloids, including those used as viscosity agents but excluding those used as bulking agents and carrageenans, can be present in the composition in an amount less than 100% by weight of the amount of iota carrageenan, desirably in an amount less than or equal to the amount of kappa carrageenan, and most desirably in an amount less than 2% by weight of the composition. The total amount of all hydrocolloids, including the carrageenans but excluding bulking agents, desirably does not exceed 22% by weight of the composition.

The film-forming composition comprises a bulking agent, such as a modified starch. The bulking agent increases the solids content of the film-forming composition, thereby contributing to a reduction in the amount of energy and time necessary to dry the film-forming composition once formed into a capsule or capsule shell. The bulking agent desirably is a low viscosity modified starch that contributes only minimally to gel formation, but serves to increase film strength and sealability of the film-forming composition, and reduces water content in the wet formulation. Further, the bulking agent provides some adhesiveness, minimizes syneresis of the kappa carrageenan, improves seam formation and increases viscosity of the film-forming composition. Desirably, the bulking agent is a low viscosity esterified starch as known to practitioners in the art, such as but not limited to N-LOK® (starch sodium octenyl succinate), a modified waxy maize starch with corn syrup solids added, sold by National Starch & Chemical Company of Bridgewater, N.J. Desirably, the modified starch is corn or maize based. Optionally, up to 30% of the modified starch can be replaced with conventional unmodified starch and/or modified pregelatinized starch such as, but not limited to, Ultra Sperse® M by National Starch and Chemical Company of Bridgewater, N.J. The film-forming composition has a weight ratio of bulking agent to total carrageenan of from about 1:1 to about 20:1, and desirably from about 2:1 to about 15:1. The bulking agent comprises from about 10% to about 60% by weight of the total film-forming composition and desirably from about 15% to about 50% by weight of the total film-forming composition. Those skilled in the art will recognize other bulking agents, such as but not limited to modified pregelatinized starch, guar gum, gum arabic and locust bean gum, can be used in the composition. However, hydrolyzed starches and dextrins are not recommended for use in the composition.

The film-forming composition further comprises one or more plasticizer selected from those known to practitioners in the art. A plasticizer provides extensibility and improved sealability in the film-forming composition, allowing for formation of strong seams during encapsulation of a dosage form. Also, plasticizers reduce the tensile strength of films made from the film-forming composition. A desirable plasticizer is a combination of sorbitol and maltitol, most desirably a combination of a non-crystallizing sorbitol, such as SORBITOL SPECIAL™ acquired from SPI Polyols of New Castle, Del., and LYCASIN®, a maltitol acquired from Roquette of Keokuk, Iowa. Non-crystallizing sorbitol is desirable over regular sorbitol because regular sorbitol is believed to cause blooming in capsules, a defect where white crystals form on the surface of capsules during storage. Acceptable substitutes for non-crystallizing sorbitol include other plasticizers as known to practitioners in the art, such as but not limited to glycerin, polyethylene glycol and combinations thereof. The amount of plasticizer used in the film-forming composition is from about 10% to about 50% by weight of the total film-forming composition, and desirably from about 12% to about 36% by weight of the total film-forming composition.

The film-forming composition comprises water in an amount sufficient to bring the total composition to 100% by weight. Generally, water is present in an amount from about 10% to about 90% by weight of the composition. Desirably, water is present in an amount of from about 14% to about 79% by weight of the composition, and more desirably from about 20% to about 60% by weight of the composition. It is desirable that the water is distilled water. If the film-forming composition is used to form medicinal, nutritional or other softgels or caplets intended for human use or consumption, purified distilled water is desirable.

As known to practitioners in the art, the film-forming composition can also contain other ingredients, such as taste modifiers, opacifying and coloring agents, preservatives, and similar additives that do not significantly alter film-forming capabilities. The additives can be added in any amount known to practitioners in the art to achieve the desired effect without altering the film-forming properties of the composition. Desirably, the total amount of all additives does not exceed 5% by weight of the composition, more desirably, it does not exceed 2% by weight of the composition.

The solids content of the wet film-forming composition is from about 11% to about 90% by weight of the wet composition, desirably from about 40% to about 90% by weight, most desirably from about 50% to about 80% by weight of the wet composition.

The desired physical characteristics of the wet film-forming composition are based upon the encapsulation of dosage forms using encapsulation machinery as known to practitioners in the art. One method of capsule production known in the art uses a rotary die process in which a molten mass of a gelatin film-forming composition is fed from a reservoir onto cooled drums to form two spaced sheets or ribbons in a semi-molten state. These sheets are fed around rollers and brought together at a convergent angle into the nip of a pair of roller dies that include opposed die cavities. A dosage form is fed into the wedge-shaped joinder of the sheets. The sheets are continuously conveyed between the dies, with the dosage form to be encapsulated, such as a medicament, being trapped between the sheets inside the die cavities. The sheets are then pressed together ("sealed"), and severed around each die so that opposed edges of the sheets seal together to encapsulate or enrobe the dosage form, forming a capsule. The part of the sheet that is severed from the segments forming the capsules is collected and either discarded or recycled, depending on the content of the dosage form. The capsules are dried to increase the film integrity and packaged for later distribution and sale. Other encapsulating machines and methods applicable for use with the film-forming composition described herein are known to practitioners in the art, such as but not limited to the method of enrobing hard tablets (SOFLET™) as disclosed and claimed in U.S. Pat. Nos. 5,146,730 and 5,549,983.

To form a capsule using the film forming composition described herein, the film-forming composition is first formed by mixing all materials together and heating with stirring until a smooth liquid, free of particulates, is formed. Desirably, the hydrocolloids comprising kappa and iota carrageenan are mixed together with a bulking agent and any other dry optional ingredients. A plasticizer is added with mixing to the dry mix. Water is then added with continued mixing and the entire mixture is heated until the ingredients are uniformly dispersed. Additives such as colorants, opacifiers, preservatives, flavorants and the like as known to practitioners in the art can be added as desired during the mixing process.

In one embodiment, all the dry ingredients (kappa carrageenan, iota carrageenan, and bulking agent, as well as dry additives) are blended together to form a dry mix. In a separate container, water and plasticizer, as well as any liquid additives, are mixed together as a liquid mix and heated to at least about 75° C., desirably about 90° C. While stirring the hot liquid mix, the dry mix is slowly added to the hot liquid mix to minimize formation of large lumps. The dispersion formed is heated with mixing to a temperature of from about 85° C. to about 95° C. The temperature is maintained with mixing until the film-forming composition melts to form a smooth liquid free of particulates.

The film-forming composition in liquid form can be subjected to one or more treatments as known to practitioners in the art. The treatments can include casting the liquefied composition into a ribbon or sheet, drying the ribbon, and conditioning it to a predetermined moisture content, typically from about 5% to about 20% moisture by weight of the ribbon, preferably from about 5% to about 15% moisture by weight of the ribbon, as known to practitioners in the art. The dry ribbon or sheet can be stored, or used directly after drying. Desirably, the dry ribbon or sheet is used to encapsulate a dosage form, such as by use of a rotary die encapsulation machine, although other methods of encapsulation as known to practitioners in the art may also be used. Alternatively, the film-forming composition can be cast into a wet film on the drum of a rotary die encapsulation machine and the wet film used to encapsulate a dosage form. Encapsulated dosage forms include, but are not limited to drug dosage forms, nutritional supplements, cosmetics, bath oils and gels, paint balls and the like.

The film-forming composition can also be formed by adding a dry mix and a liquid mix as defined elsewhere herein to an extruder, wherein the dry and liquid mixes are mixed together and heated, then extruded through dies into sheets, films or tubes. A premixed film-forming composition may also be added to an extruder for extrusion to form sheets, films or tubes. The extruded composition is fed to an encapsulation machine for the manufacture of encapsulated dosage forms. Encapsulated dosage forms include, but are not limited to drug dosage forms, nutritional supplements, cosmetics, bath oils and gels, paint balls and the like.

As used herein, the term "sheet" or "ribbon" is meant to include any form of the film-forming composition suitable for encapsulation of a dosage form as known to practitioners in the art, including but not limited to sheets, films, tubes, hemispheres, cones and the like. Wet cast or extruded ribbons are desirably from 0.4 mm to about 1.0 mm thick, though other thicknesses can be formed and used as known to practitioners in the art. Dry ribbons are typically from about 0.5 mm to about 0.7 mm thick, though thicker or thinner dry ribbons can be formed as known to practitioners in the art. The thickness of a dry or wet ribbon is determinable by a practitioner in the art based on the desired end use. Desirably, the moisture content of the dry ribbon is from about 5% to about 20% by weight of the ribbon, more desirably from about 5% to about 15% by weight of the ribbon.

Once the film-forming composition is formed into the desired shape, it can be used to encapsulate dosage forms including liquids, solids, gels and suspensions, according to methods known to practitioners in the art. Typically, for encapsulation, the film-forming composition is heated to and maintained at a temperature of from about 60° C. to about 100° C., desirably from about 75° C. to about 95° C., during the encapsulation process. For example, when a rotary die encapsulation machine is used, the film-forming composition is heated by a wedge that is located above the dies. The film-forming composition is maintained at a temperature of from about 60° C. to about 99° C., typically from about 75° C. to about 95° C., during encapsulation of the dosage form. Other examples of equipment, heating methods and temperatures therefore are known to practitioners in the art.

During encapsulation, the ribbon is frequently lubricated to prevent adherence to the machinery and prevent entrapment of air bubbles within the capsule. Suitable lubricants are known to practitioners in the art, and include, but are not limited to, triglycerides, mineral oil and acetylated monoglycerides.

Once formed, the capsule shell of dry film-forming composition desirably has a solids content of from about 80% to about 95% by weight of the dry composition. Iota carrageenan is present in an amount of from about 2% to about 20% by weight of the dry composition, and desirably from about 2.5% to about 10% by weight of the dry composition. Kappa carrageenan is present in an amount of from about 0.4% to about 20% by weight of the dry composition, and desirably from about 0.5% to about 10% by weight of the dry composition. The bulking agent is present in an amount of from about 10% to about 80% by weight of the dry composition, and desirably from about 40% to about 70% by weight of the dry composition. The plasticizer is present in an amount of from about 15% to about 40% by weight of the dry composition, and desirably from about 20% to about 30% by weight of the dry composition. The water content is from about 2% to about 10% by weight of the dry composition, and desirably from about 5% to about 7% by weight of the dry composition.

EXAMPLES

Examples of film-forming compositions of the invention are set forth below. Composition components are set forth by weight percentage of the total weight of the composition; "ι" refers to iota carrageenan and "κ" refers to kappa carrageenan.

Kappa and iota carrageenan are standardized carrageenan (standardized with maltodextrin) supplied by TIC Gums of Belcamp, Md. Standardized kappa carrageenan is supplied as TIC PRETESTED® COLLOID 710H. Standardized iota carrageenan is supplied as TIC PRETESTED® COLLOID 881M. The modified starch is N-LOK®, starch sodium octenyl succinate with corn syrup solids added, and the modified pregelatinized starch is Ultra Sperse® M, both supplied by National Starch and Chemical Company of Bridgewater, N.J. SORBITOL SPECIAL® is non-crystallizing sorbitol supplied by SPI Polyols of New Castle, Del. The maltitol used is LYCASIN®, supplied by Roquette of Keokuk, Iowa. Glycerin is USP GLYCERIN acquired from commercial sources such as Henkel of Cincinnati, Ohio. Titanium dioxide is supplied by Warner-Jenkinson Co., Inc., of South Plainfield, N.J. Water is purified, distilled water prepared inhouse.

| EXAMPLE 1 | |
| --- | --- |
| Kappa Carrageenan | 2.0% |
| Iota Carrageenan | 2.0% |
| Modified Starch | 20.0% |
| Ratio of starch:total carrageenan | 5:1 |
| Sorbitol Special ™ | 36.0% |
| Distilled Water | 40.0% |

| EXAMPLE 2 | |
| --- | --- |
| Kappa Carrageenan | 2.0% |
| Iota Carrageenan | 2.0% |
| Modified Starch | 15.0% |
| Ratio of starch:total carrageenan | 7.5:2 |
| Sorbitol Special ™ | 35.0% |
| Titanium Dioxide | 0.5% |
| Distilled Water | 45.5% |

| EXAMPLE 3 | |
| --- | --- |
| Kappa Carrageenan | 1.0% |
| Iota Carrageenan | 3.0% |
| Modified Starch | 20% |
| Ratio of starch:total carrageenan | 5:1 |
| Sorbitol Special ™ | 30.0% |
| Titanium Dioxide | 1.0% |
| Distilled Water | 45.0% |

| EXAMPLE 4 | |
| --- | --- |
| Kappa Carrageenan | 2.0% |
| Iota Carrageenan | 3.0% |
| Modified Starch | 20% |
| Ratio of starch:total carrageenan | 4:1 |
| Sorbitol Special ™ | 35.0% |
| Titanium Dioxide | 0.5% |
| Distilled Water | 39.5% |

| EXAMPLE 5 | |
| --- | --- |
| Kappa Carrageenan | 1.5% |
| Iota Carrageenan | 2.5% |
| Modified Starch | 20.0% |
| Ratio of starch:total carrageenan | 5:1 |
| Glycerin (USP) | 25.0% |
| Titanium Dioxide | 0.5% |
| Distilled Water | 50.5% |

| EXAMPLE 6 | |
| --- | --- |
| Kappa Carrageenan | 1.5% |
| Iota Carrageenan | 2.5% |
| Modified Starch | 20.0% |
| Ratio of starch:total carrageenan | 5:1 |
| Maltitol | 25.0% |
| Titanium Dioxide | 0.5% |
| Distilled Water | 50.5% |

| EXAMPLE 7 | |
| --- | --- |
| Kappa Carrageenan | 1.5% |
| Iota Carrageenan | 2.5% |
| Modified Starch | 20.0% |
| Ratio of starch:total carrageenan | 5:1 |
| Glycerin (USP) | 12.5% |
| Sorbitol Special ™ | 12.5% |
| Titanium Dioxide | 0.5% |
| Distilled Water | 50.5% |

| EXAMPLE 8 | |
| --- | --- |
| Kappa Carrageenan | 1.5% |
| Iota Carrageenan | 2.5% |
| Modified Starch | 25.0% |
| Ratio of starch:total carrageenan | 6.25:1 |
| Maltitol | 5.0% |
| Sorbitol Special ™ | 15.0% |
| Titanium Dioxide | 0.5% |
| Distilled Water | 50.5% |

| EXAMPLE 9 | |
| --- | --- |
| Kappa Carrageenan | 2.5% |
| Iota Carrageenan | 2.5% |
| Modified Starch | 23.0% |
| Ratio of starch:total carrageenan | 4.6:1 |
| Maltitol | 16% |
| Sorbitol Special ™ | 8% |
| Titanium Dioxide | — |
| Distilled Water | 48% |

| EXAMPLE 10 | |
| --- | --- |
| Kappa Carrageenan | 1.5% |
| Iota Carrageenan | 3.5% |
| Modified Starch | 25.0% |
| Ratio of starch:total carrageenan | 5:1 |
| Maltitol | 7.0% |
| Sorbitol Special ™ | 13.0% |
| Titanium Dioxide | 0.10% |
| Distilled Water | 49.90% |

| EXAMPLE 11 | |
| --- | --- |
| Kappa Carrageenan | 1.5% |
| Iota Carrageenan | 3.5% |
| Modified Starch | 25.0% |
| Ratio of starch:total carrageenan | 5:1 |
| Maltitol | 8.0% |
| Sorbitol Special ™ | 15.0% |
| Titanium Dioxide | 0.10% |
| Distilled Water | 46.90% |

-continued

EXAMPLE 12

| | |
|---|---|
| Kappa Carrageenan | 2.5% |
| Iota Carrageenan | 2.5% |
| Modified Starch | 40.0% |
| Pregelatinized Starch | 5.0% |
| Ratio of starch:total carrageenan | 9:1 |
| Maltitol | 3.75% |
| Sorbitol Special ™ | 18.75% |
| Titanium Dioxide | — |
| Distilled Water | 27.50% |

The film-forming compositions of examples 1–12 were cast into films and dried to between about 5% and about 15% moisture. The films were cut into strips 20 mm wide by 50 mm long. The films for Examples 2–12 were tested for tensile strength at rupture and extensibility using a TA-XT2 Texture Analyzer manufactured by Stable Micro Systems, (Surrey, UK). The following table charts the tensile strength and extensibility of the resulting films, where the values are mean values with standard deviations taken from four (4) replicates.

TABLE 1

| Example # | Tensile Strength at Rupture (N) | Maximum Extension at Rupture (mm) |
|---|---|---|
| 2 | 10.7 ± 0.2 | 53.1 ± 3.3 |
| 3 | 14.8 ± 0.7 | 63.6 ± 4.7 |
| 4 | 12.9 ± 0.5 | 45.7 ± 2.1 |
| 5 | 5.8 ± 0.4 | 43.2 ± 1.6 |
| 6 | 13.2 ± 1.2 | 51.4 ± 2.2 |
| 7 | 7.1 ± 0.6 | 45.9 ± 8.3 |
| 8 | 15.6 ± 2.4 | 64.9 ± 5.7 |
| 9 | 10.3 ± 0.3 | 42.4 ± 2.2 |
| 10 | 29.7 ± 2.0 | 56.6 ± 2.0 |
| 11 | 18.7 ± 4.5 | 41.4 ± 9.2 |
| 12 | 29.5 ± 0.6 | 59.8 ± 7.2 |

To demonstrate the desirable characteristics for kappa carrageenan, iota carrageenan and bulking agents used in this invention, commercially available kappa carrageenan, iota carrageenan and a modified starch were formed into solutions and their viscosity, gel point, melting point and gel strength were measured. The materials used were as follows:

Kappa Carrageenan: Colloid 710H (Lot #1025) from TIC Gums of Belcamp Md.
Iota Carrageenan: Colloid 881M (Lot #1539) from TIC Gums of Belcamp Md.
Modified Starch (starch sodium octenyl succinate): N-Lok (Lot #FK17502) from National Starch & Chemical Co. of Bridgewater, N.J.

Procedure:

A 3% dispersion of carrageenan in purified distilled water was prepared by heating the water to 70° C. and adding the carrageenan with stirring. The dispersion was heated at 70° C. until it became smooth and free of any particulates (non-dispersed carrageenan). Similarly, a 10% dispersion of modified starch in water was prepared.

The viscosity, gelling, holding, frequency and heating (melting) profiles were measured using a mechanical rheometer (AR1000 Advanced Mechanical Rheometer manufactured by TA Instruments of New Castle, Del.) using a 4° steel cone. Viscosity was measured by shearing the sample at a rate of 0 to 120 per second in two (2) minutes.

The gelling profile was determined by dropping the temperature from 80° C. to 10° C. at 5° C. per minute, with constant strain and frequency of 2% and 1 Hz, respectively. The gelling point was determined to be the temperature at which the storage and loss moduli, G' and G" respectively, crossed. Following gelling, the sample was held at 10° C. for 5 min to obtain a holding profile. After the holding step, the mechanical spectrum (frequency profile) of the gel formed was determined by performing a frequency sweep from 0.1 Hz to 100 Hz at 10° C., with constant strain of 2%. The storage modulus (G') at a frequency of 1 Hz was chosen as the gel strength of the gel formed by the carrageenan dispersion. The gel was then heated at a rate of 5° C. per minute from 10° C. to 95° C. to obtain the melting profile of the gel, with constant strain and frequency of 2% and 1 Hz, respectively. The melting point was determined to be the temperature at which the storage and loss moduli, G' and G" respectively, crossed. The results are set forth in Table 2.

TABLE 2

| Sample | Viscosity (cP) | Gelling point (° C.) | Melting point (° C.) | Gel Strength (Pa) |
|---|---|---|---|---|
| 3% kappa carrageenan dispersion in water | 618.4 | 40.6 | 60.3 | 35,740 |
| 3% iota carrageenan dispersion in water | 93.8 | 61.2 | 64.9 | 976 |
| 1.5% kappa carrageenan + 1.5% iota carrageenan dispersion in water | 206.6 | 47.2 | 70.8 | 19,800 |
| 10% starch sodium octenyl succinate | 3.8 | — | — | — |

The above results are within the desirable ranges for viscosity, gel point, melting point and gel strength for iota carrageenan, kappa carrageenan and a bulking agent. Desirably, the range for these parameters for dispersions of iota carrageenan, kappa carrageenan and a bulking agent as described above are as set forth below in Table 3.

TABLE 3

| Sample | Viscosity (cP) | Gelling point (° C.) | Melting point (° C.) | Gel Strength (Pa) |
|---|---|---|---|---|
| 3% kappa carrageenan dispersion in water | 580–650 | 38–43 | 57–64 | 33,000–38,000 |
| 3% iota carrageenan dispersion in water | 85–100 | 58–65 | 60–69 | 920–1,100 |
| 1.5% kappa carrageenan + 1.5% iota carrageenan dispersion in water | 190–220 | 44–50 | 67–75 | 18,000–21,000 |
| 10% starch sodium octenyl succinate | 3–5 | — | — | — |

Although specific embodiments of the present invention have been described in detail, it is to be expressly understood that the invention is not limited thereto. The above detailed description of embodiments of the invention is provided for example only and should not be construed as limiting the invention. Modifications and substitutions will be apparent to those skilled in the art, and all modifications and substitutions that do not depart from the spirit of the invention are intended to be included within the scope of the appended claims.

What is claimed is:

1. A method for preparing a film-forming composition comprising:
   a) mixing iota carrageenan in an amount of from about 1% to about 15% by weight of the composition, kappa carrageenan in an amount less than 100% by weight of the iota carrageenan and a bulking agent in a ratio of bulking agent to total carrageenan of from about 1:1 to about 20:1 to form a dry mixture;

b) mixing a plasticizer and water to form a liquid mixture;

c) heating the liquid mixture to a temperature of from about 75° C. to about 90° C.;

d) adding the dry mixture to the heated mixture with stirring to form a dispersion; and e) heating the dispersion with stirring to a temperature of from about 85° C. to about 95° C. to form a uniform dispersion.

2. The method of claim 1, further comprising casting a ribbon with the uniform dispersion.

3. The method of claim 2, further comprising feeding the ribbon into a rotary die encapsulation machine.

4. The method of claim 2, further comprising drying the ribbon to a moisture content of from abut 5% to about 20%.

5. The method of claim 4, further comprising feeding the dried ribbon into a rotary die encapsulation machine.

6. The method of claim 1, further comprising extruding the uniform dispersion.

7. The method of claim 6, wherein the extruded uniform dispersion is in the shape of a film, ribbon, sheet or tube.

8. The method of claim 7, further comprising feeding the extruded uniform dispersion into a rotary die encapsulation machine.

\* \* \* \* \*